US005562675A

United States Patent [19]
McNulty et al.

[11] Patent Number: 5,562,675
[45] Date of Patent: Oct. 8, 1996

[54] APPARATUS FOR SIZING A FEMORAL COMPONENT

[75] Inventors: Donald E. McNulty, Warsaw; David C. Kelman, Winona Lake, both of Ind.; John R. Moreland, Pacific Palisades, Calif.; John E. Hamm, Warsaw, Ind.

[73] Assignee: DePuy Inc., Warsaw, Ind.

[21] Appl. No.: 437,848

[22] Filed: May 9, 1995

Related U.S. Application Data

[62] Division of Ser. No. 937,704, Sep. 1, 1992, Pat. No. 5,445,642.

[51] Int. Cl.$^6$ ............................................. A61B 17/56
[52] U.S. Cl. .............................. 606/96; 606/102; 606/88
[58] Field of Search ............................. 606/87, 88, 102, 606/86, 82, 80, 96, 79; 623/18, 20

[56] References Cited

U.S. PATENT DOCUMENTS

| | | |
|---|---|---|
| 4,474,177 | 10/1984 | Whiteside . |
| 4,487,203 | 12/1984 | Androphy . |
| 4,567,886 | 2/1986 | Petersen . |
| 4,646,729 | 3/1987 | Kenna et al. . |
| 5,035,700 | 7/1991 | Kenna . |
| 5,053,037 | 10/1991 | Lackey . |
| 5,122,144 | 6/1992 | Bert et al. . |
| 5,133,759 | 7/1992 | Turner . |

FOREIGN PATENT DOCUMENTS 538153  4/1993  European Pat. Off. .

OTHER PUBLICATIONS

Schutt, Jr., "Total Knee Arthroplasty Using the F.I.R.S.T.™ Instruments and the Synatomic™ Total Knee System", Flexible Integrated Replacement Surgical Technique, DePuy Brochure, 1985, pp. 1–22.

Buechel, "New Jersey LCS® Total Knee System—Performance in Motion", Surgical Procedure, DePuy Brochure, 1989, pp. 1–35.

Hack et al., "Surgical Procedure—The Omnifit® STAT-IM™ Surgical Instruments", Osteonics Corp., 1991, pp. 1–26.

"Surgical Technique for the AGC® total Knee System", ACCU-LINE™ Knee Instrumentation, Biomet, Inc. Brochure, 1990, pp. 1–18, Author unknown.

Yoshioka et al., "The Anatomy and Functional Axes of the Femur", Journal of Bone and Joint Surgery, vol. 69–A, No. 6, Jul. 1987, pp. 873–880.

"Surgical Procedure for the Whiteside Ortholoc® Modular Knee System", Dow Corning Wright Brochure, 1990, pp. 1–38, Author unknown.

Scott, et al., "P.F.C.® Modular Knee System with Specialist® Instruments", Surgical Technique, Johnson & Johnson Orthopaedics, date unknown, pp. 1–97.

Insall et al., "Insall/Burstein® II Constrained Condylar Modular Knee System", Surgical Technique using Zimmer® Intramedullary Instrumentation, The Hospital for Special Surgery, date unknown, pp. 1–32.

"Zimmer Intramedullary Knee Instrumentation for the Miller/Gallante Total Knee System", Zimmer, Inc. brochure, 1986.

*Primary Examiner*—Michael Powell Buiz
*Assistant Examiner*—Guy V. Tucker
*Attorney, Agent, or Firm*—Barnes & Thornburg

[57] ABSTRACT

A sizing assembly for determining the optimum size of a femoral component of a knee prosthesis is placed against the resected distal end of a femur. The assembly includes a body with a flat surface for contacting the resected surface of the femur and feet for engaging the femoral condyles. The assembly further includes a pivoted stylus that slides in the body and engages the anterior femoral cortex. Once the size of the femoral component is determined, a drill bushing corresponding to the femoral component is supported on the body. The drill bushing includes two apertures for guiding a drill to bore pilot holes in the resected femur.

5 Claims, 8 Drawing Sheets

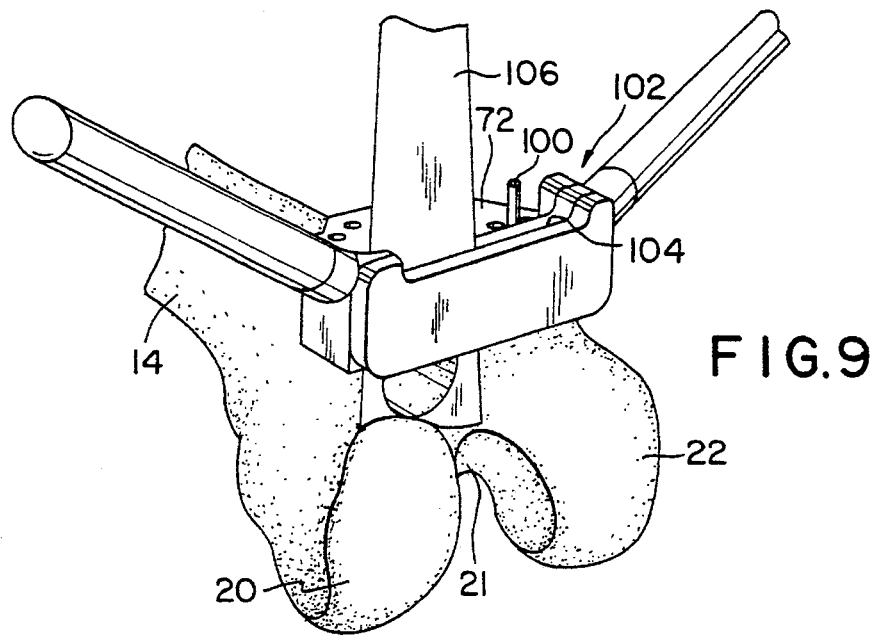
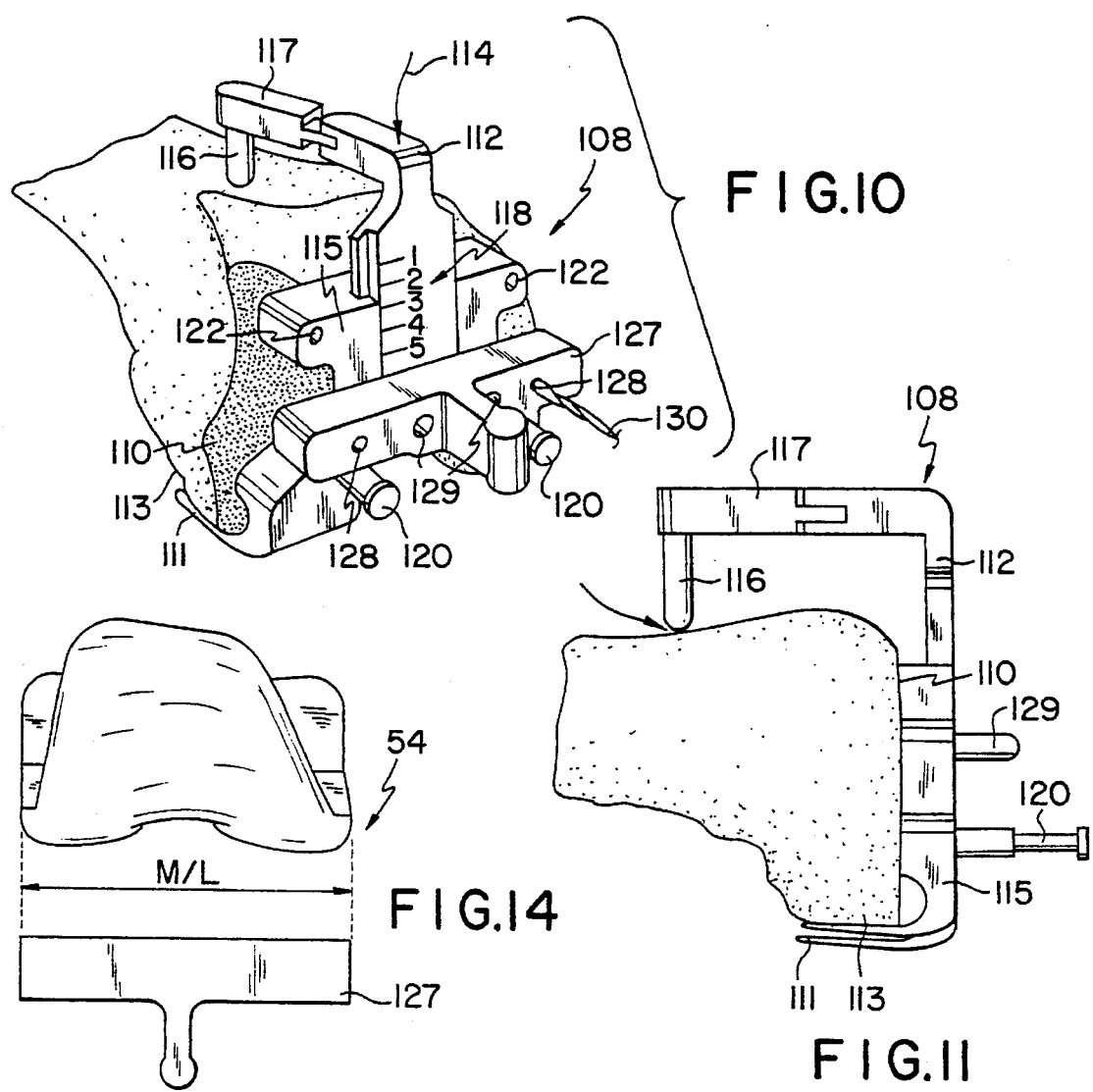

| TABLE I | | | | |
|---|---|---|---|---|
| | Lateral Condyle Thickness | | Component Distal Thickness | |
| | To IC Notch | IC Notch +3mm Resect | Size | mm |
| Small | 4 mm | 7 mm | 1 2 | 6 7 |
| Medium | 6 mm | 9 mm | 3 4 | 8 9 |
| Large | 8.4 mm | 11.4 mm | 5 | 10 |

APPARATUS FOR SIZING A FEMORAL COMPONENT

This is a divisional application of application Ser. No. 07/937,704 filed Sep. 1, 1992, now U.S. Pat. No. 5,445,642.

BACKGROUND AND SUMMARY OF THE INVENTION

The present invention relates to a method for reconstructing a femoral portion of a knee in a total knee replacement of both the medial and lateral condyles. More particularly, the present invention relates to a method in which the femoral component of reconstructed knee presents both the lateral and medial condyles at substantially the same distal position as the original natural lateral condyle to locate the intercondylar notch and distal patellar groove in a position generally coinciding with the natural intercondylar notch and distal patellar groove being replaced.

The proximal/distal placement of the femoral component in total knee arthroplasty is critical for duplicating the kinematics of the knee with the arthroplasty. Several authors have recommended that the joint line (transverse axis) of the arthroplasty should be at approximately the same proximal/distal position as the joint line (transverse axis) of the normal knee. Most surgical techniques recommend that an amount be resected off the distal femur roughly equal to the thickness of the femoral prosthesis, doing so will restore the joint line to substantially its original position. This is actually too simplistic an analysis of a complex situation. For example, sometimes there is wear of the distal condyles and osteophytes can deform the distal condyles. Thus, the original cartilage covered surface, which represents the original distal femoral surface, is usually not available for referencing at the time of surgery. More importantly, the average transverse axis (joint line) is tilted 3° with respect to the mechanical axis of the knee. This is because the medial femoral condyle is more distally placed than the lateral femoral condyle in the normal knee. Most authorities today recommend that the transverse axis of the reconstruction be made perpendicular to the mechanical axis. Thus, the original transverse axis is tilted 3° and the reconstructed transverse axis is made perpendicular to the mechanical axis.

In an arthritic valgus knee the medial femoral condyle is usually much more distally placed than the lateral femoral condyle due to wear or lateral femoral condyle hypoplasia. In an arthritic varus knee there has usually been some wear of the medial femoral condyle, but in most cases, despite this wear, the medial femoral condyle is still more distally placed than the lateral femoral condyle. In both varus and valgus knees the reference condyle for distal femoral resection is presently the medial condyle.

The distal femur actually has three different surfaces for articulation. There is the medial femoral condyle, the lateral femoral condyle, and the central portion of the distal femur against which articulates the patella. The distal femur, obviously, has articulating against it both the tibia and the patella. The proximal/distal placement of the patella/femoral joint is just as important, and perhaps even more important, than the proximal/distal placement of the tibial/femoral joint.

If a surgeon has an 8 mm thick femoral component and resects 8 mm off the distal medial femoral condyle, in almost all knees the surgeon resects several millimeters less of distal lateral condyle. If the surgeon then installs an 8 mm femoral component, the knee has a lengthened lateral femoral condyle and a lengthened intercondylar notch which defines the patella/femoral joint line. In other words, the new joint line has been placed at approximately the level of the original medial femoral condyle but has been placed distally with respect to the original lateral femoral condyle.

This lengthening of the lateral femoral condyle requires the patella to move more distally with respect to the femur as the patella moves to the distal aspect of the femur in the extremes of flexion. This requires more stretching of the quadriceps mechanism and higher patella load. This may make the patella more likely to dislocate and increase the likelihood of subluxation. The higher patella load may also be the cause of some lateral pain and may contribute to patella fractures.

In contrast to the above known method, the present invention reconstructs the distal joint surface of the knee at approximately the distal level of the original lateral femoral condyle. One advantage of reconstructing the knee at the level of the original lateral femoral condyle is that it gives more room for the tibial component. The tibial base plate should be adequately thick for strength and the tibial plastic bearing insert should be adequately thick for wear considerations. There is a problem with space in the reconstruction. If a surgeon lengthens the lateral femoral condyle it aggravates the space problem. Reconstructing the knee at the level of the lateral femoral condyle leaves more room for a tibial component and minimizes the tibial resection level. In addition, a thicker plastic tibial bearing may be used with the present invention. As the thickness of the bearing increases, internal stresses tend to decrease.

The instruments of the present invention resect 3 mm of bone from the intercondylar notch area preferably using the notch as a reference point. Each femoral component of the present invention is approximately three millimeters thick in the patellar groove area, regardless of the size of the component. Therefore, the distal patellar groove of the prosthetic femoral component of the present invention is anatomically positioned at about the same distal position as the groove in the normal knee. Accordingly, the patella must travel only its original distal excursion distance during normal knee flexion.

Of course, large bones have deeper notches than small bones since bones are proportionately sized. A three millimeter depth of resection in the notch area in a small bone will remove less distal femoral condyle than a three millimeter depth of resection in the intercondylar area for a large bone. The present invention provides a plurality of femoral components having distal femoral condyles which gradually become thicker with size proportionally to compensate for the varying amounts of the distal femoral condyles which are resected.

The present invention preferably uses the intercondylar notch as a reference point for guiding resection of the distal end of the femur. The notch reference is not affected by condyle hypoplasia which can occur both to the medial and the lateral femoral condyle and it is typically not affected by wear of an individual condyle. The notch area is rarely worn, although occasionally osteophytes do form that need to be resected. In the valgus knee with a hypoplastic lateral femoral condyle the notch area is not hypoplastic. The lateral femoral condyle resection level in such cases gives the desired lengthening of the lateral femoral condyle in that type of knee. Referencing the intercondylar notch for proximal/distal placement of the femoral component consistently and accurately reconstructs the patella/femoral joint at its appropriate proximal/distal level. This results in the tibial/ femoral component joint being reconstructed at also its proper proximal/distal level but without the problems of severe anatomical variations and severe bony erosion. The notch reference point is a more convenient and reliable reference point for proximal/distal placement of the femoral component than the distal femoral condyle reference point.

Another issue which relates to this is the rotational position of the femoral component. The medial femoral condyle is larger than the lateral femoral condyle and for proper femoral rotation, usually a larger piece of bone needs to be resected off the posterior medial femoral condyle than the posterior lateral femoral condyle. This results in a relatively more externally rotated position of the femoral component with respect to the femur and provides better patella tracking. The patella tracks better with this maneuver and is less likely to dislocate and the knees flex better and are more stable. Fewer lateral releases are needed and fewer revisional surgeries are needed for patellar subluxation and dislocation. The instruments of the present invention have a built-in 3° of external rotation.

The method and apparatus of the present invention involves resecting the distal medial and lateral condyles in a plane generally perpendicular to the mechanical axis of the femur at a predetermined distance proximal to the intercondylar notch preferably using the notch as a reference. Then a femoral component is selected to have a size and thickness to present both the medial and lateral condyles at the same general distal position as the original natural lateral condyle being replaced. This selecting step involves selecting an appropriate size femoral component from a group of components having varying sizes and condyle thicknesses.

The present invention preferably uses the intercondylar notch as a reference point for distal condylar resection. However, it is understood that other reference points can be used in order to reestablish the patella femoral groove at the same location as the natural knee and to reestablish the medial and lateral condyles at the same general distal position as the original natural lateral condyle being replaced. The reference points include the medial condyle and the lateral condyle as well as the intercondylar notch.

It is not new to use the intercondylar notch as a reference point for distal condylar resection per se. Prior art systems have used the notch as a reference point from which to make the distal condylar resection. For instance, in one system designed by Buechel & Pappas, the first resection is a resection of the proximal end of the tibia to provide a tibia platform. This resection is made with typical tibial instrumentation. Then, the anterior and posterior femur condyles are resected independent of the notch. Then, referencing the intercondylar notch, Buechel & Pappas resect the distal end of the femur.

Other systems including DePuy's F.I.R.S.T. system introduced in mid-1980s also use the intercondylar notch as a reference point for making the distal femoral resection, but this system does not try to reconstruct the natural lateral condyle being replaced. Also, in DePuy's F.I.R.S.T. system, the femoral implants were not proportioned in size and thickness to place both the medial and lateral condyles of the natural distal position generally corresponding to the original lateral condyle.

The present invention involves selecting a femoral component to place both the medial and lateral condyles at the same level, but at the same level as the original lateral condyle. The method of the present invention therefore, is an advancement over the prior art methods and apparatus because the new method recreates the lateral condyle joint line versus the medial condyle joint line. The present invention reestablishes the original natural distal patellar groove in which the patellar articulates at the same general position as the natural distal patellar groove. This improvement places less strain, wear and tear on the patellar tendon and potentially reduces soft tissue releases for proper tracking of the patellar mechanism.

It is an object of the present invention to provide a method for reconstructing a femoral portion of a knee in a total knee replacement of both the medial and lateral condyles so that the reconstructed knee presents the lateral and medial condyles at the same general distal position as the original natural lateral condyle and locates the intercondylar notch and distal patellar groove in a position generally coinciding with the natural notch and groove.

According to one aspect of the present invention, a method is disclosed for reconstructing a femoral portion of a knee in a total knee replacement of both the medial and lateral condyles to locate the intercondylar notch and distal patellar groove of the reconstructed knee in a position generally coinciding with the natural intercondylar notch and distal patellar groove. The method includes the steps of resecting the distal medial and lateral condyles to form a resected distal surface, selecting a femoral component sized to have an intercondylar notch and distal patellar groove at the same general distal position as the original natural intercondylar notch and distal patellar groove being replaced, and installing the selected femoral component on the resected distal surface.

In the illustrated embodiment, the plane of the resected distal surface is generally perpendicular to the mechanical axis of the femur. The resected distal surface is spaced apart a predetermined distance proximal from the intercondylar notch using the intercondylar notch as a reference. However, other reference points may be used.

The femoral component has a thickness in the area of a patellar groove substantially equal to said predetermined distance so that the distal patellar groove of the femoral component is positioned at substantially the natural location of the distal patellar groove. The selecting step includes the steps of providing a plurality of femoral components having various anterior/posterior lengths and increasing distal and posterior condyle thicknesses as the anterior/posterior length increases and determining which of the plurality of femoral components has an appropriate distal and posterior condyle thickness to approximate the natural distal position of the resected lateral condyle.

According to another aspect of the present invention, a method is disclosed for reconstructing a femoral portion of a knee in a total knee replacement of both the medial and lateral condyles so that both the medial and lateral condyles of the reconstructed knee are located at about the same distal position as the original natural lateral condyle. The method includes the steps of resecting the distal medial and lateral condyles to form a resected distal surface, selecting a femoral component sized to have both the medial and lateral condyles at the same general distal position as the original natural lateral condyle being replaced, and installing the selected femoral component on the resected distal surface.

The selecting step includes the step of providing a plurality of femoral components having various anterior/posterior lengths and increasing distal and posterior condyle thicknesses as the anterior/posterior length increases and determining which of the plurality of femoral components has an appropriate distal and posterior condyle thickness to approximate the natural distal position of the resected lateral condyle. The determining step illustratively includes the step of placing a sizer assembly on the resected end of the femur to indicate which one of the plurality of femoral components is appropriately sized for the resected femur.

The resected distal surface is spaced apart a predetermined distance proximal from the intercondylar notch. The femoral component has a thickness in the area of a patellar groove substantially equal to said predetermined distance so that the distal patellar groove of the femoral component is positioned at substantially the natural location of the distal patellar groove.

According to yet another aspect of the present invention, a method is provided for reconstructing a femoral portion of a knee in a total knee replacement, the distal end of which has medial and lateral condyles and an intercondylar notch therebetween defining a distal patellar groove for the articulation of the patella with the femur during flexion of the knee. The method includes the steps of locating and drilling a hole in the intercondylar notch to access an intermedullary canal of a femur, installing a femoral alignment guide onto an intermedullary rod, and inserting the intermedullary rod through said hole toward a proximal end of the femur. The method also includes the steps of moving said femoral alignment guide into contact with the intercondylar notch of the knee, positioning a femoral cutting block relative to the alignment guide, and securing the cutting block to the femur to align a guide surface of the cutting block at a predetermined proximal distance from said intercondylar notch. The method further includes the steps of removing the femoral alignment guide and rod from the femur, resecting the distal lateral and medial condyles using the guide surface of the resection block as a resection reference, and determining an appropriate size of a femoral component having a size and condyle thickness which will reconstruct the lateral condyle and position the distal patellar groove at about the same distal locations to approximate the anatomy of the natural knee being replaced and to position the medial condyle of the femoral component at the same distal position as the original lateral condyle.

In the one illustrated method, the step of moving the femoral alignment guide into contact with the intercondylar notch of the knee includes the step of positioning an intercondylar saddle on the alignment guide in engagement with the intercondylar notch. The step of positioning the femoral cutting block relative to the alignment guide includes the step of positioning the cutting block on an arm of the alignment guide at a selected position spaced apart from the intercondylar saddle by predetermined distance so that the femur is resected a predetermined distance proximal to the intercondylar notch. The step of determining an appropriate size of a femoral component includes the step of placing a sizer assembly on the resected distal end of the femur to determine an appropriate size femoral component.

According to still another aspect of the present invention, an alignment guide is provided for positioning a saw guide surface of a cutting block at a predetermined position proximally from an intercondylar notch of a femur having an intermedullary rod extending along its anatomical axis. The alignment guide includes a body portion formed to include an aperture for receiving the rod therethrough, and an arm coupled to the body for receiving the cutting block thereon. The alignment guide also includes means for securing the cutting block to the arm at a predetermined position relative to the body, and an intercondylar saddle coupled to the body portion of the alignment guide, the saddle being configured to engage the intercondylar notch of the femur to align the cutting block coupled to the arm of the alignment guide at said predetermined position proximal to the intercondylar notch.

The saddle is configured to surround the aperture for receiving the intermedullary rod. The saddle permits limited movement of the alignment guide relative to the intermedullary rod to permit the alignment guide to be seated at the deepest section of the intercondylar notch. The saddle includes a first generally U-shaped stop for engaging the intercondylar notch located above the aperture a second generally U-shaped stop for engaging the intercondylar notch located below the aperture.

The alignment guide further includes a calibrated stop pivotably coupled to the body portion. The calibrated stop is movable from a first position abutting the arm to align the guide surface of the cutting block a predetermined distance from the saddle to establish said predetermined position relative to the intercondylar notch to a second position to permit the position of the cutting block to be adjusted.

According to a further aspect of the present invention, a sizer assembly is provided for determining the optimum size femoral component to couple to a resected distal end of a femur from a group of femoral components having various sizes and condyle thicknesses. The assembly includes a body portion including a flat contact surface for engaging the resected end of the femur, a plurality of feet coupled to a bottom surface of the body for engaging posterior femoral condyles to align the body portion with the resected distal end of the femur, and a stylus assembly slidably coupled to the body portion. The stylus assembly includes an arm extending proximally away from the body portion and a stylus coupled to the arm. The stylus assembly is movable relative to said body portion until the stylus engages the anterior femoral cortex. The sizer assembly also includes means on the stylus assembly and body portion for indicating the size of femoral component corresponding to the resected femur based on the position of the stylus assembly relative to the body portion. The sizer assembly further includes means coupled to the stylus assembly for supporting a drill bushing thereon corresponding to the size of the femoral component indicated by the indicating means.

The supporting means aligns the drill bushing relative to the anterior femoral cortex. The arm the drill bushing includes first and second apertures for guiding a drill to bore pilot holes in the resected femur for securing the femoral component to the resected femur.

According to a still further aspect of the present invention, an assembly is provided for aligning a cutting block relative to a resected distal end of a femur. The assembly includes a body portion having a flat contact surface for engaging the resected end of the femur, and a plurality of feet coupled to a bottom surface of the body for engaging posterior femoral condyles to align the body portion with the resected distal end of the femur. The assembly also includes a stylus assembly slidably coupled to the body portion. The stylus assembly includes an arm extending proximally away from the body portion and a stylus coupled to the arm. The stylus assembly is movable relative to said body portion until the stylus engages the anterior femoral cortex. The assembly further includes means coupled to the stylus assembly for aligning a cutting block on the resected distal end of the femur relative to the anterior femoral cortex.

According to an additional aspect of the present invention, a method is provided for reconstructing a femoral portion of a knee in a total knee replacement, the distal end of which has medial and lateral condyles and an intercondylar notch therebetween defining a distal patellar groove for articulation of the patella with the femur during flexion of a knee. The method includes the steps of securing a body portion to the distal end of the knee. The body portion is coupled to an intermedullary rod located within an intermedullary canal of a femur. The method also includes the steps of coupling a first cutting guide to the body portion, moving the first cutting guide relative to the body portion to align a guide slot of the first cutting guide at a selected location, resecting an anterior surface of the femur through the guide slot of the first cutting guide, and removing the first cutting guide from the body portion. The method further includes the steps of coupling a second cutting guide to the body portion, adjusting the position of the second cutting guide relative to the body portion to align a guide slot of the second cutting guide a predetermined distance from the intercondylar notch, securing the second cutting guide to the resected anterior portion of the femur, and cutting the distal end off the femur using the guide slot of the second cutting guide as a reference so that the femur is resected a predetermined distance proximally from the position of the intercondylar notch. The method still further includes the step of determining an appropriate size of a femoral component having a size and condylar thickness which will reconstruct the intercondylar notch at about the same distal position as the natural intercondylar notch.

The step of adjusting the position of the second cutting guide relative to the body portion includes the step of aligning a notch formed in the second cutting guide with the intercondylar notch. The guide slot of the second cutting guide is spaced said predetermined distance from the notch.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

FIG. 9 is a perspective view illustrating a saw capture coupled to the resection block for guiding a saw blade to resect the distal end off the femur.

FIG. 10 is a perspective view illustrating a sizing apparatus coupled to the resected distal end of femur for determining an appropriate size femoral component to install on the end of the femur.

FIG. 11 is a side elevational view of the sizing apparatus illustrated in FIG. 10.

FIG. 14 is a diagrammatical view illustrating a femoral component and a drill bushing of the present invention.

DETAILED DESCRIPTION OF THE DRAWINGS

In total knee arthroplasty the goal is to provide pain free mobility to the patient. This is accomplished by resurfacing the tibia, femur, and the patella. Reconstruction of the knee requires the reestablishment of two joint lines, the tibial/femoral joint line and the patella/femoral joint line. Great attention has typically been paid to the reconstruction of the tibial/femoral joint line.

Figure 1:
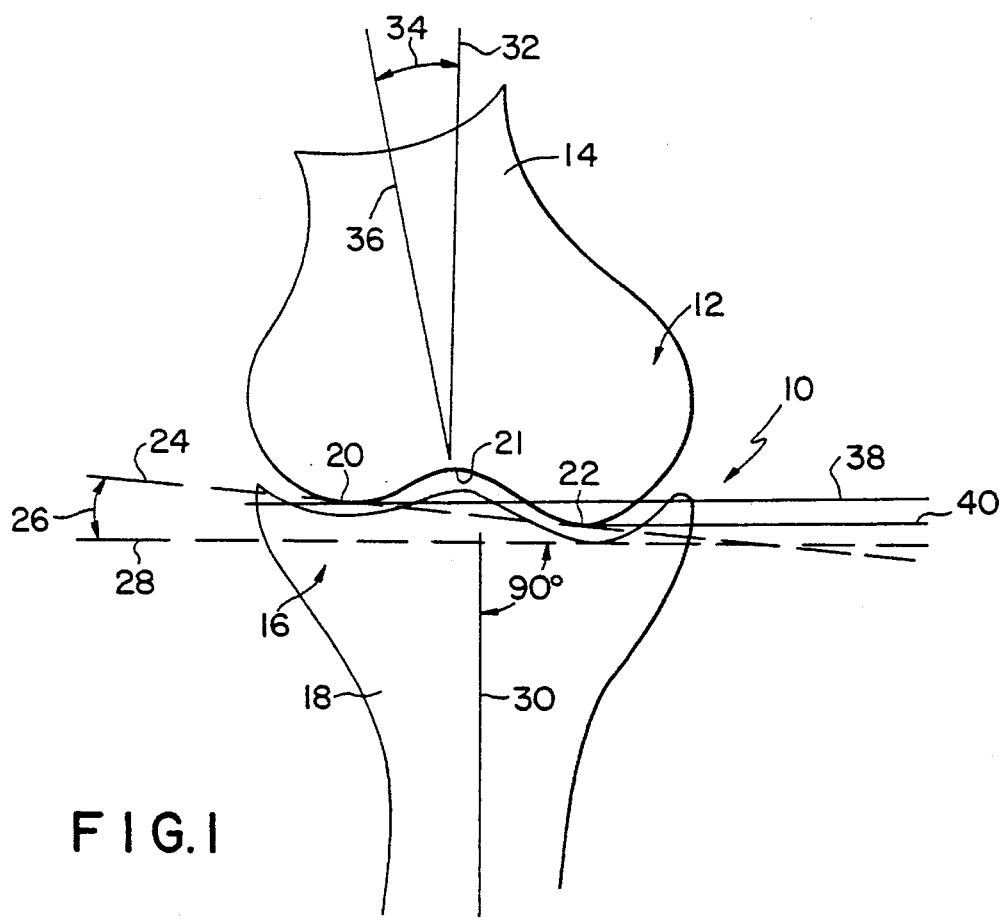
FIG. 1 is a diagrammatical view illustrating various joint lines of a knee.

As illustrated in FIG. 1, a knee joint 10 is established between a distal end 12 of femur 14 and proximal end 16 of tibia 18. The distal end 12 of femur 14 includes a lateral condyle 20 and a medial condyle 22. The lateral and medial condyles 20 and 22 articulate against a superior articulate surface of the tibia 18. Engagement of the lateral and medial condyles 20 and 22 with the superior surface of tibia 18 establishes a joint line 24 which is aligned at about a 3° angle 26 relative to the plane 28 perpendicular to the mechanical axis 30 of tibia 18. Tibia 18 is usually resected about plane 28 during total knee arthroplasty.

Femur 14 includes a mechanical axis 32 and an anatomical axis 36 aligned at about a 6° angle 34 relative to mechanical axis 32. The tibial/femoral joint 24 is established, provided that the tibia is resected with a 3° of varus slope. Although, currently, most surgeons resect the proximal tibia at 90° to axis 30 of the tibia 18. This results in the creation of two joint lines. A surgeon can recreate the medial joint line 40 or the lateral joint line 38. Instrumentation that references off of the medial condyle reconstructs the medial condylar joint line 40. During flexion of the knee, the patella articulates with the lateral condyle and not the medial condyle.

Reestablishment of the tibial/femoral joint has typically been accomplished in prior art methods by instrumentation that references off the distal medial condyle 22 as illustrated by reference line 42 in FIG. 2. A fixed amount of bone is resected from the distal medial condyle 22 corresponding to the thickness of the femoral component 46 installed distal end 12 of femur 14. Normally 6 to 10 mm is resected as illustrated by resection line 44.

In prior knee reconstruction methods, a fixed amount of distal resection is typically made regardless of the size of the femur. This is because all of the femoral components have been designed with constant distal and posterior thicknesses, regardless the size of the implant. The present invention includes a set of femoral components having increasing distal and posterior thicknesses as the size of the implant increases. Anthropometric data indicates that as the femur increases in the A/P and M/L dimensions, the size or thickness of the distal and posterior condyles also increases. The distance from the distal medial and lateral condyles to the intercondylar notch increases distally as the A/P dimension of the femur increases.

Therefore if a constant distal resection is made regardless of the size of the femur this will result in excess bone being removed from small knees and in insufficient bone being removed from large knees. For small male femurs the thickness of the distal lateral condyle from the intercondylar is approximately 4 mm and for large male femurs the thickness is approximately 8.4 mm. A constant distal resection of 8 mm will place the femoral component in a different location depending upon the size of the femur. This then results in the shifting the patella/femoral joint line proximally in small femurs and distally in large femurs.

Figure 2:
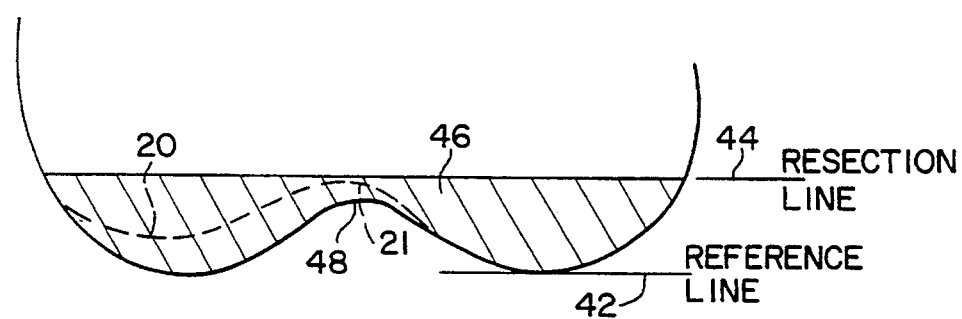
FIG. 2 is a diagrammatical illustration of prior art methods for replacing the medial and lateral condyles with a femoral component.

By referencing from the medial condyle and resecting the same amount of bone from the reference line 42, prior art knee reconstruction methods illustrated in FIG. 2 include a prosthetic femoral component 46 which approximates the original position of the medial condyle 22. However, such prior art knee reconstruction methods add condyle thickness to the lateral condyle and add thickness to the intercondylar notch so that femoral component 46 extends distally beyond the natural position of the lateral condyle and the intercondylar notch. The natural position of the lateral condyle 20 and the intercondylar notch 21 are illustrated by the dotted line in FIG. 2. This extra material in the area of the lateral condyle and the intercondylar notch increases the distance that the patella must travel distally with respect to the femur as the patella moves to the distal aspect of the femur during extreme reflection. This extra tension can cause pain and may increase the likelihood of patella failures.

Figure 3:
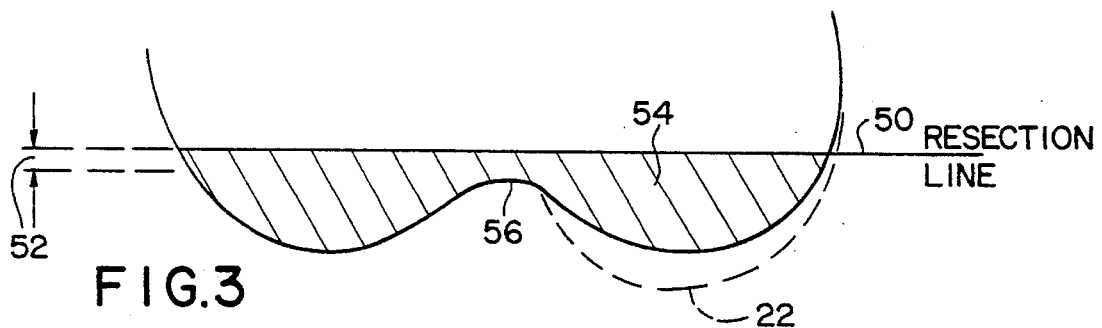
FIG. 3 is a diagrammatical illustration of the method of the present invention for replacing medial and lateral condyles with a femoral component.

The new knee construction method of the present invention is designed to more closely simulate natural movement of the patella by placing femoral component 54 at a distal position approximately equal to the distal position of the lateral condyle 20 as illustrated in FIG. 3. In addition, the method of the present invention is designed to place the groove 56 of the femoral component 46 at approximately the same position as the intercondylar notch 21. The distal end 12 of femur 12 is resected along a resection line 50 which is located a predetermined distance illustrated by dimension 52 from the position of the intercondylar notch. Distance 52 is selected to be equal to the thickness of the femoral component 54 in the area of the patellar groove 56. Therefore, when femoral component 54 is positioned on femur 12, the groove 56 of femoral component 54 is aligned at about the same distal as the natural intercondylar notch 21.

The method of the present invention does not replace the total amount of bone resected from the medial condyle 22. In other words, the medial condyle of femoral component 54 does not extend as far distally as the natural medial condyle 22. The location of natural medial condyle 22 is illustrated by dotted line 22 in FIG. 3.

An advantageous reference point for selecting the resection line 50 is the intercondylar notch 21 as discussed above. However, other reference points may be used to determine the location of resection line 50.

The instruments of the present invention reference the intercondylar notch area for proximal/distal placement of the femoral component. This reference point for proximal/distal placement is a more reliable one placing the patella/femoral joint anatomically in every knee and approximating the new joint line properly at the level of the smaller lateral distal condyle rather than the larger and usually more distally placed medial femoral condyle. This results in more space for the tibial component thus minimizing the tibial resection and allows the prosthetic patellar construct to not have to travel extra distance distally during knee flexion and thus gives a better range of motion with less problems of patellar dislocation and subluxation.

One embodiment of the method and apparatus of the present invention is illustrated in FIGS. 4–12. Preferably, the instruments of the present invention use the intercondylar notch 21 as a reference point as opposed to the medial condyle. The intercondylar notch is typically constant reference point regardless of the physical size of the femur.

In the present invention, a 3 mm resection of the intercondylar notch is made on all femurs regardless of size. The femoral components of the present invention are all approximately 3 mm thick in the intercondylar notch or patellar groove region. Thus, by removing 3 mm of bone and replacing it with 3 mm of metal, a surgeon reestablishes the distal patella/femoral joint line at substantially its natural position. This advantageously improves movement of the patella during flexion of the knee as discussed above. The amount of distal condyle resected will vary depending upon the physical size of the femur. The instruments of the present invention recreate the natural position of the lateral condyle about which the patella articulates with during flexion of the knee.

According to the first embodiment of the present invention, the distal end 12 of femur 14 is exposed in a conventional manner. A surgeon removes any osteophytes from intercondylar notch 21. In this embodiment of the invention, the intercondylar notch 21 is used as a reference point to determine the amount of distal femur that will be resected. The first step of the method is to drill and intramedullary (IM) hole in the distal end of femur 14. A femoral IM initiator drill 60 is used to create a pilot hole 62. Drill 60 has a stepped up tip 64 to hold the drill 60 at a selected entry point without "walking". Drill 60 is used only to break through the proximal cortex and to advance a short distance into the metaphysis of femur 14. For deep femoral penetration, a fluted, blunt-tipped femoral IM rod 66 is used.

Figure 4:
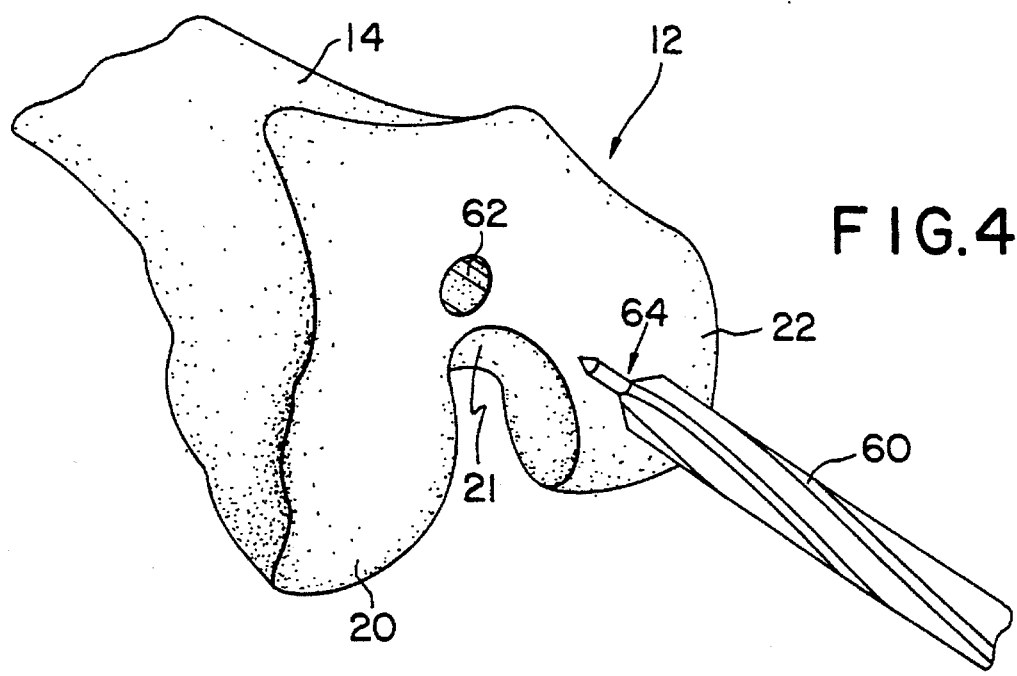
FIG. 4 is a perspective view illustrating formation of a pilot hole in the intercondylar notch of a femur.

Pilot hole 60 for IM rod 66 is positioned in the middle of the intercondylar notch 21 slightly anterior to the posterior cruciate ligament attachment as illustrated in FIG. 4. Pilot hole 62 should be in line with the anatomical axis 36 of femur 14 and should also reference off the posterior cortex of the medullary canal. Pilot hole 62 should be large enough so that hole 62 does not control the attitude of IM rod 66.

Figure 5:
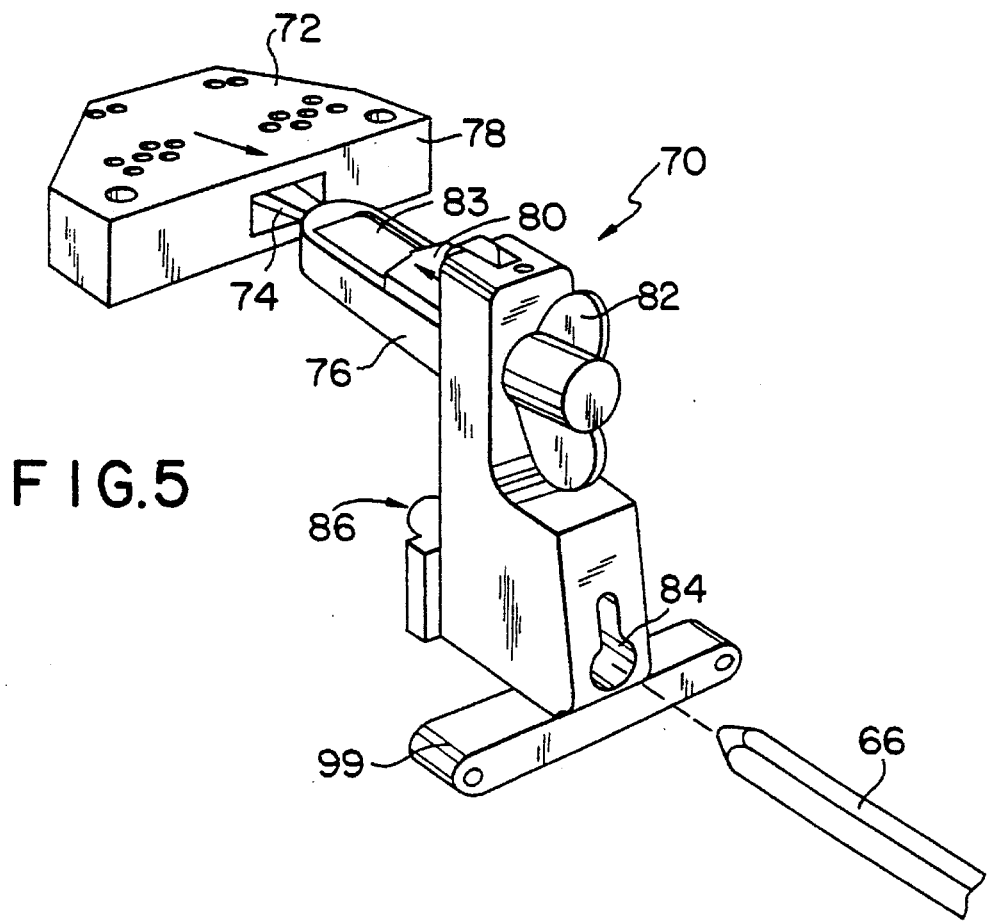
FIG. 5 is a perspective view illustrating an alignment guide and cutting block of the present invention.

FIGS. 5–8 illustrated the configuration of the femoral alignment guide 70 of the present invention. Alignment guide 70 includes a body portion 71. A 6° distal femoral cutting block 72 is coupled to alignment guide 70 as illustrated in FIG. 5. An aperture 74 of cutting block 72 is installed over arm 76 of alignment guide 70 until a guide surface 78 of cutting block 72 abuts a calibrated stop 80 on alignment guide 70. Cutting block 72 is locked into place by rotating wing nut 82 45° clockwise so the eccentric cam 83 engages cutting block 72. Cutting block 72 is configured to guide resection of distal end 12 of femur 14 with 6° of valgus inclination that is 3 mm proximal to intercondylar notch 21. In other words, guide surface 78 of cutting block 72 is aligned generally perpendicular to mechanical axis 32 of femur 14. It is understood that the angle of cutting block 72 may be changed depending upon the particular knee being reconstructed.

After cutting block 72 is installed onto alignment guide 70 and locked into place, a D-shaped femoral IM rod 66 is inserted through an aperture 84 of alignment guide 70 with a flat surface facing upwardly. IM rod is preferably 1 mm smaller than pilot hole 62 to minimize pressure build-up in the medullary canal and to allow the isthmus to dictate rod placement. Full seating of rod 66 is not necessary. The IM rod 66 is slowly advanced into the distal femur 14. Rod 66 is typically inserted to about ⅔ of its total length. The blunt tip of the IM rod 66 passes easily through the hollow shaft of the femur 14 while minimizing the chances of perforating the femoral cortex.

Figure 6:
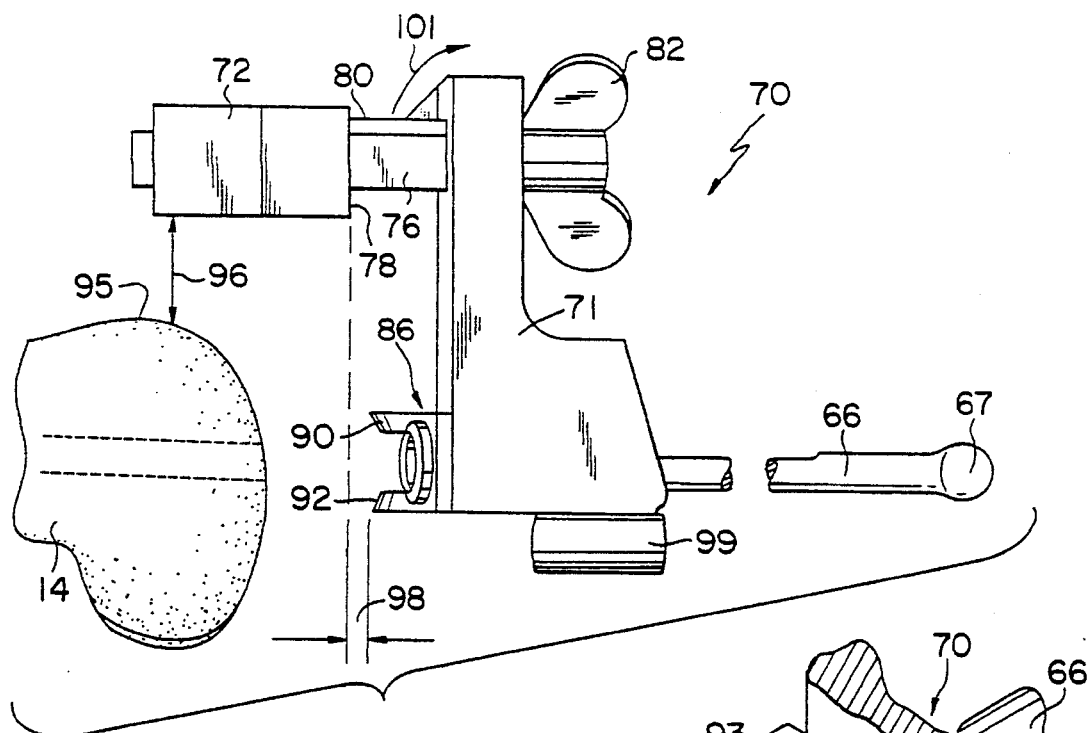
FIG. 6 illustrates the alignment guide of FIG. 5 as it is installed and positioned on the femur.
Figure 7:
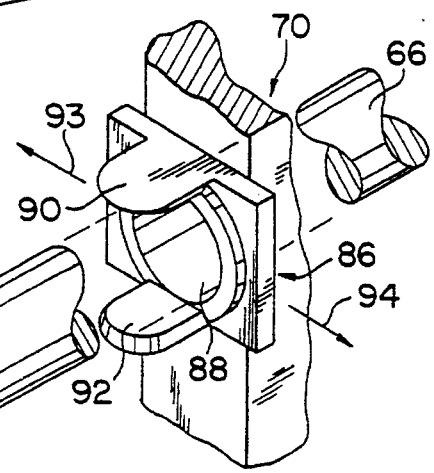
FIG. 7 is a partial perspective view of an intercondylar saddle of the alignment guide.
Figure 8:
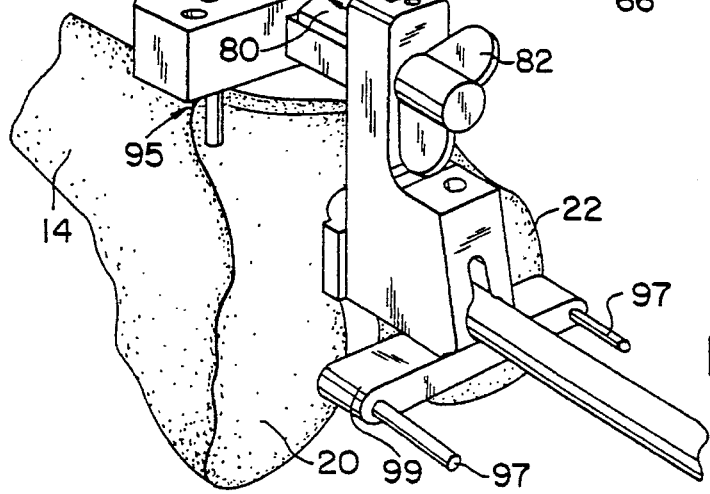
FIG. 8 is a perspective view illustrating the alignment guide fully seated against the intercondylar notch of the femur to position the cutting block relative to the femur.
Figure 12A:
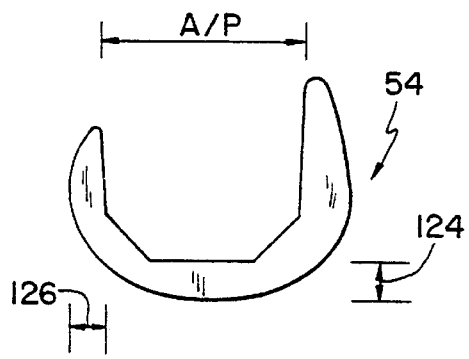
FIG. 12A–12E are diagrammatical views illustrating five different sizes of femoral components which may be selected to install on the distal end of the femur.
Figure 12B:
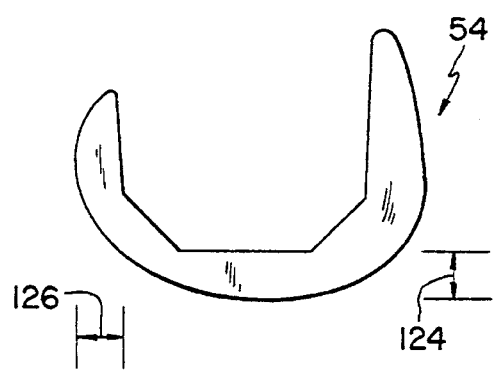
Figure 12C:
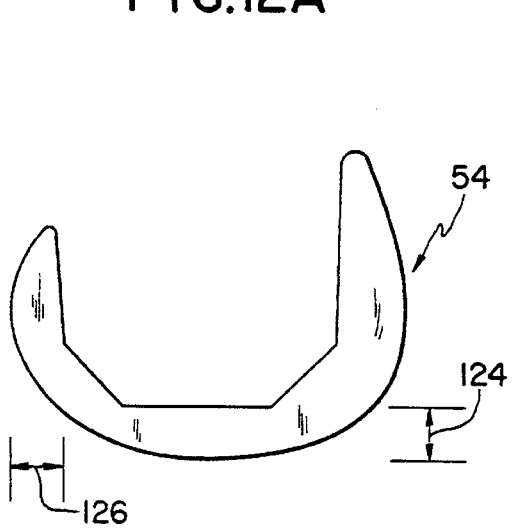
Figure 12D:
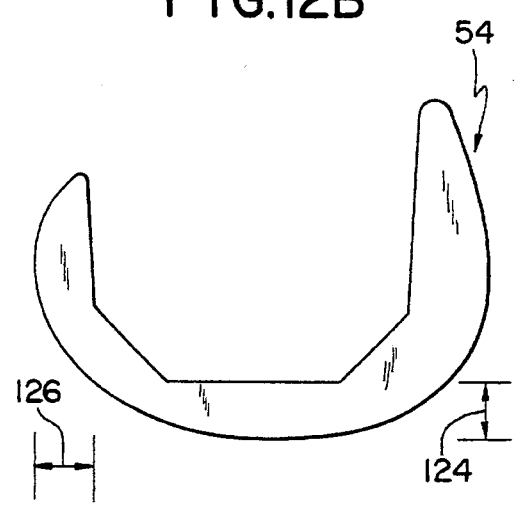
Figure 12E:
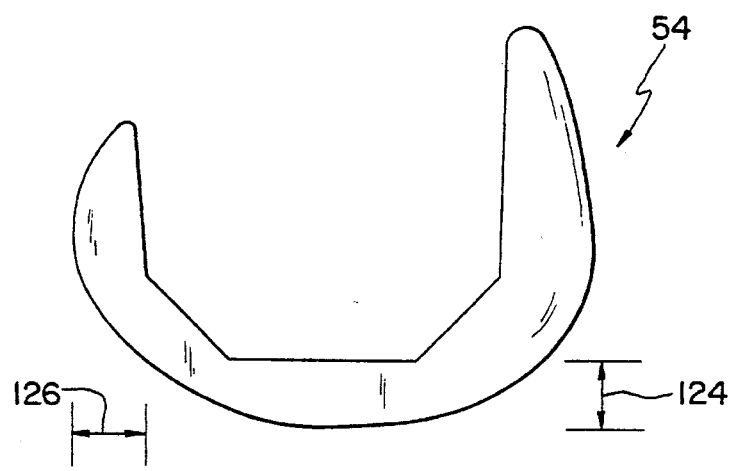

After IM rod 66 is inserted into femur 14, alignment guide 70 is moved along the longitudinal axis of rod 66 toward femur 14 until an intercondylar saddle 86 of alignment guide 70 is seated firmly in intercondylar notch 21. Saddle 86 is best illustrated in FIGS. 5–7. The intercondylar saddle 86 includes a generally circular bearing surface 88 for receiving IM rod 66 therethrough. Saddle 86 also includes an anterior generally U-shaped stop 90 located above bearing surface 88 and a posterior generally U-shaped stop 92 located below bearing surface 88. The curvature of generally U-shaped stops 90 and 92 corresponds generally to the curvature of intercondylar notch 21. Bearing 88 of saddle 86 is slightly larger than the diameter of IM rod 66 to permit limited movement of alignment guide 70 relative to IM rod 66 in the direction of arrows 93 and 94. This permits generally U-shaped stops 90 and 92 to abut the intercondylar notch despite slight misalignment of IM rod 66. This ensures that saddle 86 of alignment guide 70 is seated at the deepest section of intercondylar notch 21 for referencing resection of femur 14.

Alignment guide 70 positions cutting block 72 above the anterior surface 95 of femur 14 to provide clearance between the femur 14 and cutting block 72 as alignment guide 70 slides along rod 66 as illustrated by dimension 96 in FIG. 6. Calibrated stop 80 positions guide face 78 of cutting block 72 a predetermined distance from the front edge of U-shaped stops 90 and 92 of saddle 86 as illustrated by dimension 98. Illustratively, dimension 98 is about 3 mm which corresponds to the thickness of femoral components at the intercondylar notch area. Therefore, guide surface 78 is aligned about 3 mm proximally from the deepest part of intercondylar notch 21. Because the flat side of IM rod 66 mates with a spring-loaded plate on femoral alignment guide 70, approximate rotational alignment of guide 70 relative to femur 14 can be achieved using the T-handle 67 of IM rod 66 as a reference. For additional stability, ⅛ inch fixation pins 97 can be inserted into distal holes of visualization bar 99.

If more or less bone resection is desired, the position of the distal femoral cutting block 72 can be fine tuned. This is done by rotating wing nut 82, 45° counter clockwise to the neutral position and moving calibrated stop upwardly in the direction of arrow 100. Cutting block 72 can then slide proximally or distally on arm 76 of alignment 70. 2 mm incremental markers are provided on arm 76 for this adjustment. After the predetermined resection amount is selected, and saddle 86 is seated against intercondylar notch 21, cutting block 72 is then secured to femur 14 using a ⅛ inch drill to drill pilot holes through the center holes in cutting block 72. Two or more ⅛ inch fixation pins 100 are then extended through the holes in cutting block 72 and seated into the bone.

Alignment guide 70 is then disengaged from cutting block 72 by turning wing nut 82 to the neutral position. IM rod 66 is also removed. The cutting block then slides down fixation pins 100 until cutting block 72 contacts the anterior femur surface 95.

A surgeon may then verify the varus/valgus alignment using an external alignment tower (not shown). Correct alignment is indicated when a proximal end of an alignment rod of the tower is centered over the head of femur 14 when a distal end of the tower is positioned on cutting block 72.

After cutting block 72 is properly positioned, a saw capture 102 is coupled to cutting block 72 as illustrated in FIG. 9. Saw capture 102 includes a slot 104 for receiving a saw blade 106 therethrough. Teeth on the saw blade 106 are typically not offset, allowing the blade 106 to be inserted directly into the saw capture 102, thereby maximizing the effectiveness of saw capture 102. A drop of sterile mineral oil on saw blade 106 helps reduce friction. After the distal lateral and medial condyles 20 and 22 are resected, cutting block 72, fixation pins 100, and saw capture 102 are removed from femur 14.

As illustrated in FIGS. 10 and 11, a sizer assembly 108 is provided. Because 3° of external rotation is built into sizer assembly 108, a left and a right are provided. An appropriate sizer assembly 108 is placed flush against the resected distal femoral surface 110. Feet 111 of sizer 108 should be in direct contact with the posterior femoral condyles 113 of femur 14. Sizer assembly 108 must be centered medially and laterally since it will help determine the M/L position of the femoral component implant. Sizer assembly 108 includes a stylus assembly 112 slidable coupled to a body portion 115. Pressure is applied to stylus assembly 112 in the direction of arrow 114 until stylus 116 touches in the vicinity of the center portion of the anterior femoral cortex as best illustrated in FIGS. 10 and 11. The stylus is aligned parallel to the anatomical axis of femur 14.

After stylus 116 engages anterior femoral cortex, a surgeon can read the appropriate size femoral component directly from a calibration gauge 118 based on the relative position of stylus assembly 112 relative to body portion 115. In the example illustrated in FIG. 10, the gauge indicates that a size 3 femoral component should be selected. If the indicator gauge 118 falls between two sizes, the smaller size femoral component is typically selected. This should, however, be determined at the surgeon's discretion. When the anterior condyle cut is made for a size 3, the saw will exit at the point where the stylus touches the femur. After sizer assembly 108 is properly positioned on femur 14, a mallet is used to drive two captured fixation pins 120 into femur 14 to securely fix sizer assembly 108 to femur 14. If additional fixation is required, the sizer assembly 108 also includes anterior fixation pin holes 122 for receiving pins (not shown) therethrough.

FIGS. 12A–12E illustrate the various sizes of femoral components available for the surgeon to select based upon the reading from indicator gauge 118 of sizer assembly 108. Femoral component 54 illustrated in FIG. 12A corresponds to femoral component size 1. Femoral component 54 illustrated in FIG. 12B corresponds to femoral component size 2. Femoral component 54 illustrated in FIG. 12C corresponds to femoral component size 3. Femoral component 54 illustrated in FIG. 12D corresponds to femoral component size 4. Femoral component 54 illustrated in FIG. 12E corresponds to femoral component size 5. Each femoral component 54 has a distal condyle thickness illustrated by dimension 124 and a posterior condyle thickness illustrated by dimension 126. Dimension 124 is substantially equal to dimension 126. As the A/P dimension of the femoral components 54 increase, the thicknesses of the distal condyle 124 and the posterior condyle 126 also increase. In other words, the size 2 femoral component illustrated in FIG. 12B has distal and posterior condyle thicknesses 124 and 126 larger than the distal and posterior condyle thicknesses 124 and 126 of femoral component 54 having a size 1 illustrated in FIG. 12A.

Figures 13, 15:
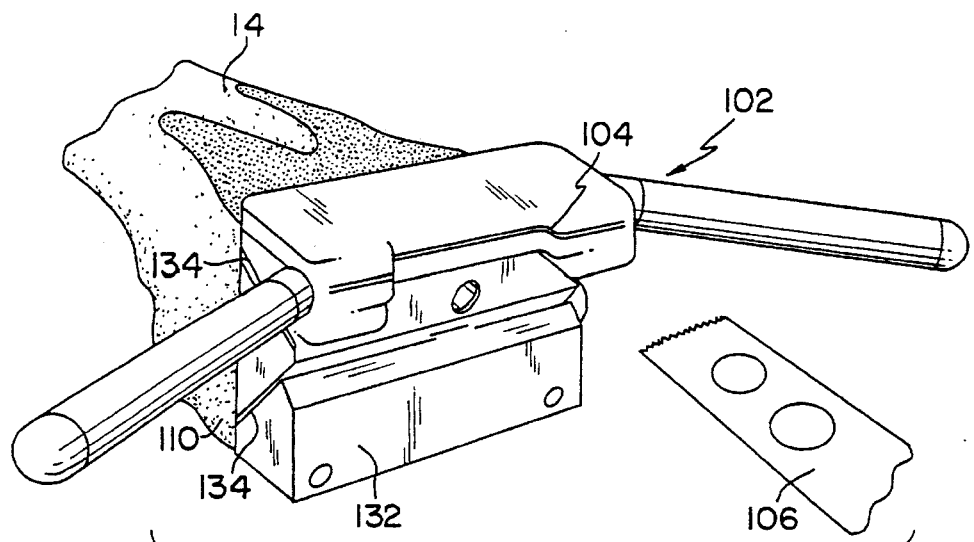
FIG. 13 is a table illustrating the natural thickness of lateral condyles on small, medium and large femurs and illustrating the distal condyle thicknesses for the various size femoral components of the present invention.
FIG. 15 is a perspective view of a resection guide and a saw capture for making further resections of the distal end of the femur.

Table I illustrated in FIG. 13 discloses the size variation of femoral components illustrated in FIGS. 12A–12E. The first column of the Table I indicates the natural lateral condyle thicknesses relative to the intercondylar notch for small, medium, and large femurs. Small femurs typically have a lateral condyle which extends about 4 mm distally from the intercondylar notch. Medium size femurs typically include lateral condyles which extend about 6 mm distally from the intercondylar notch. Large femurs typically include a lateral condyle which extends distally from the intercondylar notch by about 8. mm.

The second column of Table I indicates the distance from distal position of the natural lateral condyle to the resected surface 110 of femur 14 taking into account the 3 mm resection of the distal end of femur 14 beyond intercondylar notch 21. The third column of the Table I refers to the size of femoral component 54 used in the present invention. The fourth column of Table I refers to the distal thicknesses 124 and 126 of the distal and posterior condyles of the various size femoral components 54. For instance, the size 1 femoral component illustrated in FIG. 12A has distal and posterior condyle thicknesses 124 and 126 equal to 6 mm. For the large femoral component size 5 illustrated in FIG. 12E, the distal and posterior condyle thicknesses 124 and 126 have increased to 10 mm.

After the appropriate size femoral component 54 is selected, an appropriately sized drill bushing 127 which corresponds in size to the size of the selected femoral component is used to drill pilot holes in the resected distal end 110 of femur 14. As illustrated in FIG. 14, drill bushing 127 has a width equal to the M/L width of a corresponding femoral component 54.

Posts 129 are provided on sizer assembly 108 for receiving a drill bushing 127 thereon. Posts 129 are aligned at an angle relative to each other and have different sizes for receiving right side and left side drill bushings 127. Different size drill bushings 127 are provided for each different size of femoral component. After the appropriate size femoral component 54 is selected, a drill bushing 127 corresponding to that selected size is inserted over pegs 129 on sizer assembly 108. Sizer assembly 108 must be centered medially and laterally because it determines the M/L position of femoral component 54 on femur 14. Holes are drilled through apertures 128 in drill bushing 127 using drill 130 while maintaining light finger pressure on stylus assembly 112 in the direction of arrow 114. The holes formed by drill bit 130 are used to locate the A/P cutting blocks and femoral component 54. The drill bushing 127 is then removed from sizer assembly 108. Sizer assembly 108 is removed from femur 14 using the appropriate end of a slap hammer.

The anterior and posterior femoral condyle resections and chamfer resections are then made. An A/P cutting block 132 illustrated in FIG. 15 which corresponds to the appropriate size femoral component determined earlier is installed on the resected end 110 of femur 14. Therefore, sizer assembly 108 aligns cutting block 132 on resected distal end 110 of femur 14 relative to the anterior femoral cortex which is engaged by stylus 116. Drive pegs on the A/P cutting block 132 are inserted into the predrilled holes using a mallet. If additional fixation is needed, towel clips or ⅛ inch pins can be inserted into the holes on the side of cutting block 132. Cutting block 132 must be flush with the distal femoral cut. Anterior and posterior condyles are then resected through slot 104 in saw capture 102. The same saw capture used to resect the distal femur can be used for the anterior and posterior condyle resections. Chamfer resections are then made through slots 134 in the A/P cutting block 132. Cutting block 132 is then removed using a slap hammer (not shown). An independent anterior chamfer cutting guide also may be used. After the chamfers are cut, the distal end of the femur 114 is appropriately sized to receive the selected femoral component 54 thereon. Femoral component 54 is then installed out of the resected distal end of femur 14.

Another embodiment of the present invention is illustrated in FIGS. 16–19. In this embodiment, the anterior portion 95 of femur 14 is resected first using the cutting guide assembly 140 illustrated in FIG. 16. Cutting guide assembly 140 includes a body portion 142 configured to accept an IM rod 66. Body portion 142 can be rotated on rod 66 to align body portion 142 at a desired angle relative to the femur 14. Body portion 142 is rotated about 3° clockwise or counterclockwise depending on whether a right or left knee is being resected to provide external rotation if desired. After body portion 142 is orientated at the desired position, attachment pins 143 are driven into femur 14 to secure body portion 142 to femur 14.

A saw capture assembly 144 is slidably coupled to body portion 142. Specifically, a rod 146 coupled to saw capture assembly 144 is slidably received within an aperture of body portion 142. Therefore, saw capture assembly 144 moves up and down in the direction of double headed arrow 148 relative to body portion 142. Saw capture assembly includes a saw guide 149, an arm portion 150, and a stylus 152 extending downwardly from arm portion 150. Saw capture assembly 144 moves relative to femur 14 until stylus 152 engages the anterior femoral cortex of femur 14. A knob 154 is then rotated to secure saw capture assembly 144 in the selected position relative to body portion 142. After saw capture assembly 144 is locked in the desired position, a saw blade is used to resect anterior portion 95 off femur 14. Guide slot 155 of saw guide 149 aligns the saw blade in the proper position to resect anterior portion or 95 of femur 14.

Figures 16, 17, 18:
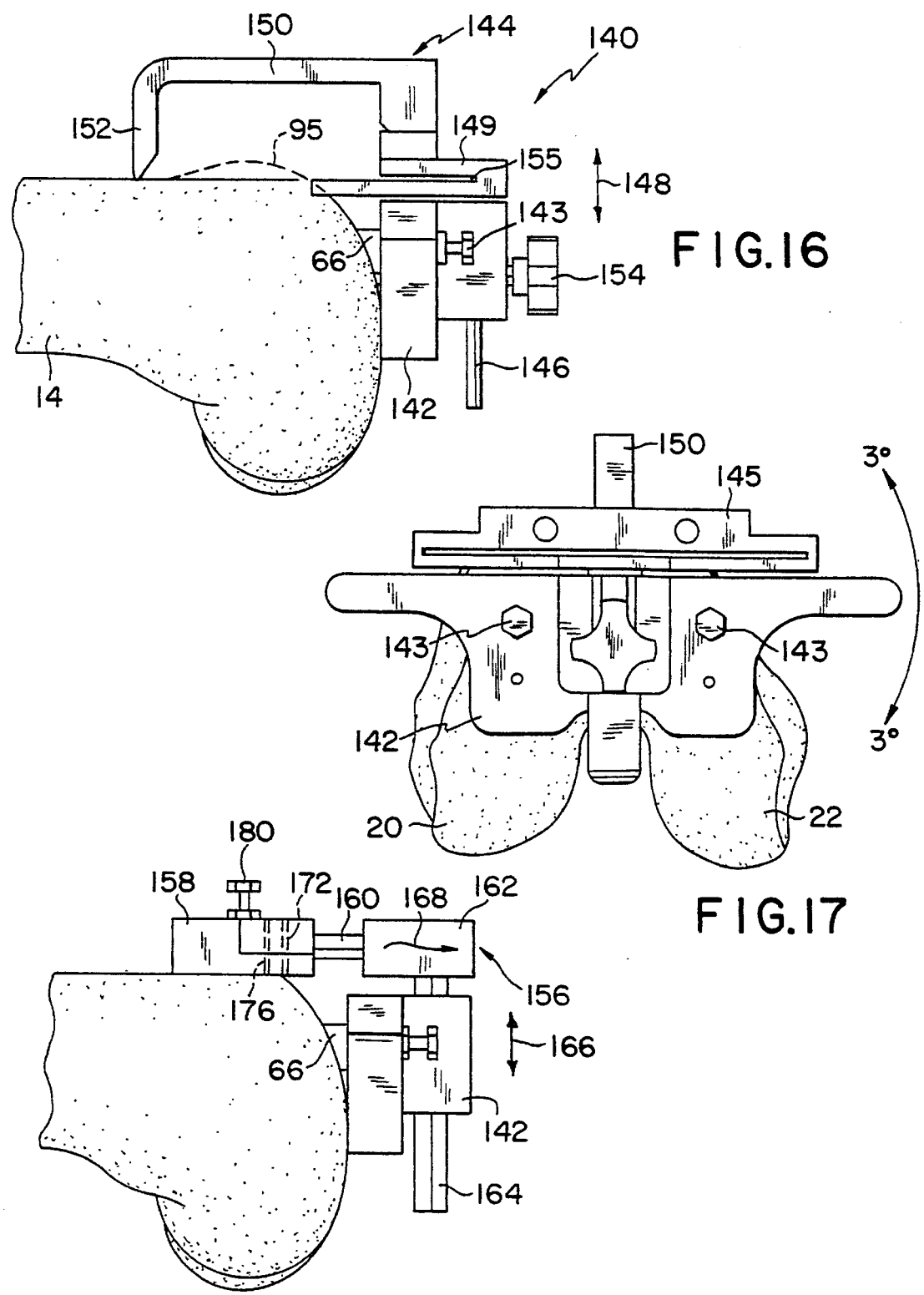
FIG. 16 is a side elevational view of a second embodiment of the present invention including a saw capture assembly for resecting an anterior portion of the femur.
FIG. 17 is an end view of the saw capture assembly illustrated in FIG. 16.
FIG. 18 is a side elevational view of a cutting block assembly for guiding a saw blade to resect the distal end of the femur.
Figure 19:
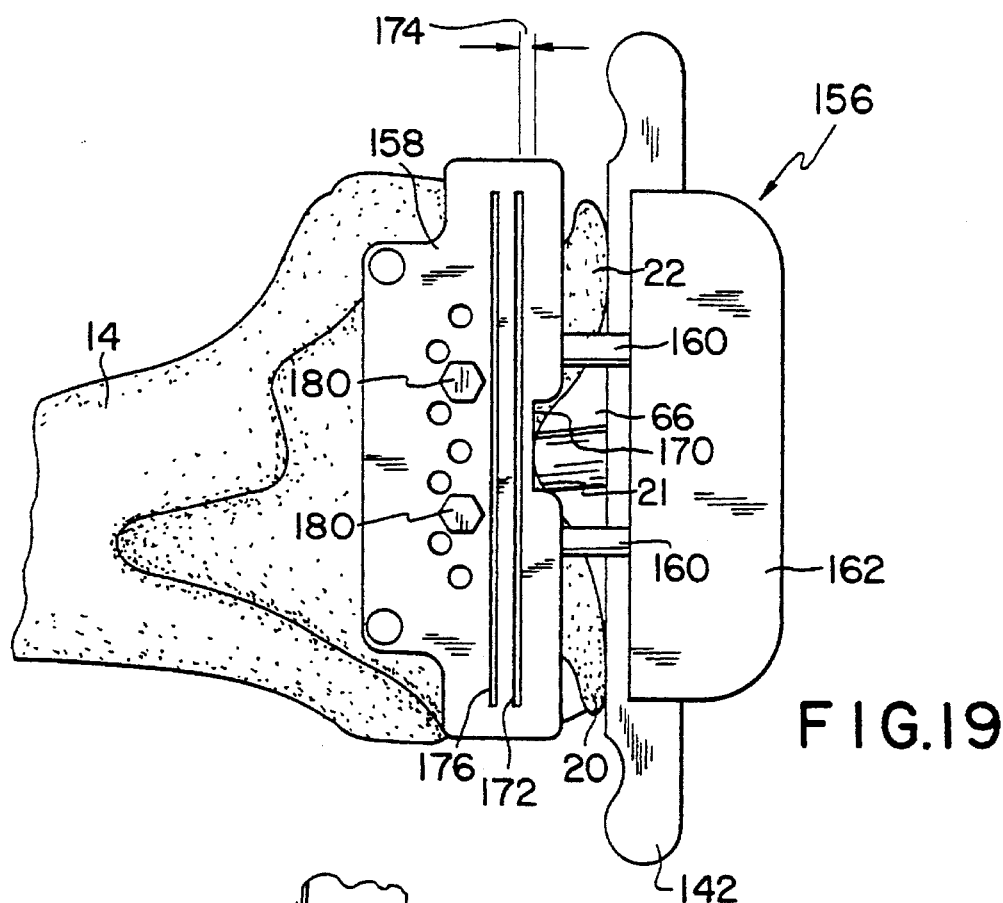
FIG. 19 is a top plan view illustrating the resection block for aligning the position of resection plane with the intercondylar notch.

Saw capture assembly 144 is then removed from body portion 142. A cutting block assembly 156 illustrated in FIGS. 18 and 19 is then inserted into body portion 142. Cutting block assembly 156 includes a cutting block 158. Posts 160 extend from cutting block 158. Posts 160 are inserted into apertures in a block 162. A post 164 is coupled to block 162. Post 164 is slidably received within the aperture of body portion 142 so that the cutting block assembly 156 can move up and down in the direction of double headed arrow 166. Cutting block 158 can also move in the direction of arrow 168 relative to block 162.

As best illustrated in FIG. 19, body portion 142 is aligned at about a 6° angle relative to rod 66. An aperture formed in body portion 142 is preferably aligned at the 6° angle. The aperture may be threaded if desired to receive a threaded rod 66. Therefore, the plane of the resection surface is aligned substantially perpendicular to the mechanical axis 32 of femur 14. A surgeon moves cutting block 158 in the direction of arrow 168 until notch 170 of cutting block 158 is aligned with intercondylar notch 21 of femur 14. Cutting block 158 includes a first saw guide slot 172 which is positioned a predetermined distance proximally from notch 170 as illustrated by dimension 174. Dimension 174 is selected to be the thickness of the femoral component 54 in the area of the intercondylar notch so that the intercondylar notch and distal patellar groove are reconstructed at approximately the same location as the natural intercondylar notch and distal patellar groove. Preferably, dimension 174 is 3 mm as in the first embodiment of the present invention. A second saw guide slot 176 is provided in case the surgeon decides additional resection of femur 14 is needed.

Figure 20:
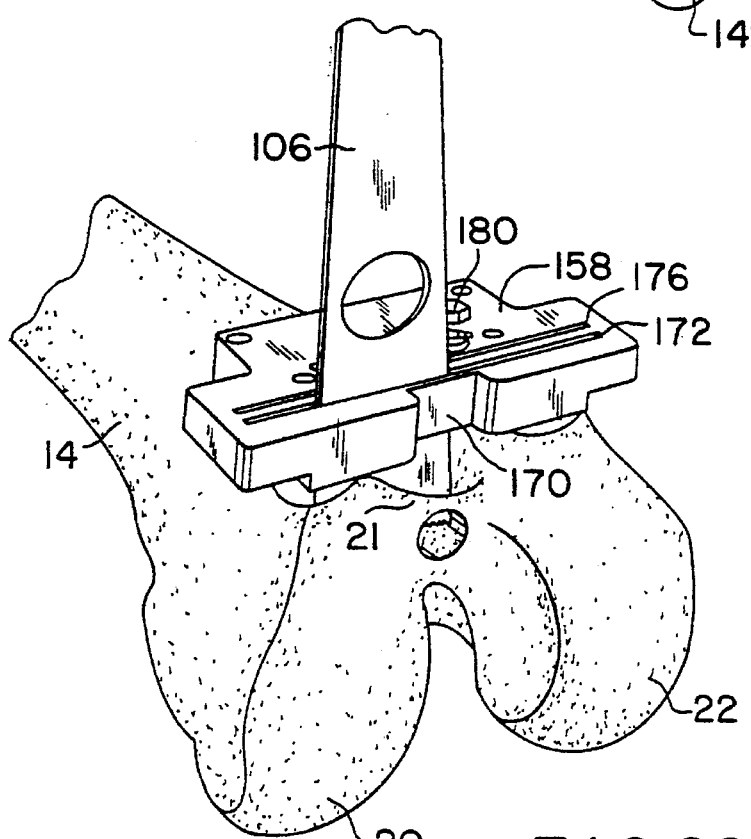
FIG. 20 is a perspective view of the resection block illustrated in FIGS. 18 and 19 with a saw blade extending through the guide slot to resect the distal end of the femur.

Resection of distal end 12 of femur 14 is best illustrated in FIG. 20. After cutting block 158 is properly aligned with intercondylar notch 21, cutting block 158 is secured to femur 14 by captured pins 180. Additional pins or screws may be used to secure cutting block 158 to femur 14 if necessary. Rod 66, body portion 142, and block 162 are then removed to permit saw blade 106 to cut the distal end off femur 14 through the previously aligned saw guide slot 172.

Although the invention has been described in detail with reference to a certain illustrated preferred embodiment, variations and modifications exist within the scope and spirit of the invention as described and defined in the following claims.

What is claimed is:

1. A sizing and drilling assembly for determining the optimum size femoral component to couple to a resected distal end of a femur from a group of femoral components having various sizes and condyle thicknesses, the assembly comprising:

a body portion including a flat contact surface for engaging the resected end of the femur;

a plurality of feet coupled to a bottom surface of the body for engaging posterior femoral condyles to align the body portion with the resected distal end of the femur;

a stylus assembly slidably coupled to the body portion, the stylus assembly including an arm extending away from the body portion and a stylus coupled to the arm, the stylus assembly being movable relative to said body portion until the stylus engages the anterior femoral cortex;

means on the stylus assembly and body portion for indicating the size of femoral component corresponding to the resected femur based on the position of the stylus assembly relative to the body portion a plurality of drill bushings of various sizes; and means coupled to the stylus assembly for supporting a drill bushing selected from the plurality of drill bushings, said selected bushing corresponding to the size of the femoral component indicated by the indicating means.

2. The assembly of claim 1, wherein the supporting means aligns the drill bushing relative to the anterior femoral cortex.

3. The assembly of claim 1, wherein each drill bushing includes first and second apertures for guiding a drill to bore pilot holes in the resected femur for securing the femoral component to the resected femur.

4. The assembly of claim 1, wherein the arm of the stylus assembly is pivotable so that the stylus is parallel to the anatomical axis of the femur.

5. The assembly of claim 1, further comprising first and second captured fixation pins coupled to the body portion for securing the body portion to the resected distal end of the femur.

* * * * *